United States Patent
Dentinger et al.

(10) Patent No.: US 8,622,913 B2
(45) Date of Patent: Jan. 7, 2014

(54) METHOD AND SYSTEM FOR NON-INVASIVE MONITORING OF PATIENT PARAMETERS

(75) Inventors: Aaron Mark Dentinger, Latham, NY (US); Kedar Anil Patwardhan, Latham, NY (US); Ralph Thomas Hoctor, Saratoga Springs, NY (US)

(73) Assignee: General Electric Company, Niskayuna, NY (US)

( * ) Notice: Subject to any disclaimer, the term of this patent is extended or adjusted under 35 U.S.C. 154(b) by 537 days.

(21) Appl. No.: 12/892,171

(22) Filed: Sep. 28, 2010

(65) Prior Publication Data

US 2012/0078106 A1    Mar. 29, 2012

(51) Int. Cl.
*A61B 8/00*    (2006.01)
(52) U.S. Cl.
USPC .......................................... 600/456; 600/441
(58) Field of Classification Search
USPC ................................................ 600/441, 456
See application file for complete search history.

(56) References Cited

U.S. PATENT DOCUMENTS

| 5,647,366 | A | 7/1997 | Weng |
| 6,535,835 | B1 | 3/2003 | Rubin et al. |
| 6,782,284 | B1 * | 8/2004 | Subramanyan et al. ...... 600/407 |
| 2003/0045795 | A1 * | 3/2003 | Bjaerum et al. .............. 600/441 |
| 2004/0066389 | A1 | 4/2004 | Skyba et al. |
| 2007/0123779 | A1 | 5/2007 | Hoctor et al. |
| 2011/0218435 | A1 * | 9/2011 | Srinivasan et al. ............ 600/441 |

FOREIGN PATENT DOCUMENTS

WO    2008/085193 A3    7/2008

OTHER PUBLICATIONS

Peter J. Brands, A. P. G. Hoeks, M. C. M. Rutten and R. S. Reneman; "A noninvasive method to estimate arterial impedance by means of assessment of local diameter change and the local center-line blood flow velocity using ultrasound"; Ultrasound in Med. & Biol., vol. 22, No. 7, pp. 895-905, 1996.

* cited by examiner

*Primary Examiner* — Jonathan Cwern
(74) *Attorney, Agent, or Firm* — Joseph J. Christian

(57) ABSTRACT

A method for continuous non-invasive monitoring of multiple arterial parameters of a patient is provided. The method includes continuously acquiring ultrasound data via an ultrasound transducer attached to the patient for detecting a blood vessel using color flow processing within a monitoring scan plane. Further, the method includes processing the continuously acquired ultrasound data to generate continuous quantitative waveforms based on an estimated cross-sectional area of the blood vessel and an estimated volumetric flow rate of blood through the vessel and displaying the generated continuous quantitative waveforms for monitoring the arterial parameters of the patient in real-time.

15 Claims, 9 Drawing Sheets

METHOD AND SYSTEM FOR NON-INVASIVE MONITORING OF PATIENT PARAMETERS

This invention was made with Government support under contract number R01HL094487 awarded by the National Institute of Health (NIH). The Government has certain rights in the invention.

BACKGROUND

The present invention relates generally to methods and system for monitoring of arterial parameters and more particularly to a method and system for continuous non-invasive monitoring of patient parameters.

Generally, non-invasive monitoring of arterial parameters is done using ultrasound measurement systems. However, continuous ultrasound measurements of cross-sectional area and volumetric flow rate of blood vessels using two-dimensional imaging are difficult to perform and typically only provide qualitative measures because of the inability to verify proper alignment of the ultrasound probe and determine the orientation of the ultrasound beam relative to the vessel. Current quantitative flow measurements use the long-axis (longitudinal) view of the vessel along with interactive measurement tools to manually correct for the Doppler angle (angle between the true blood velocity direction and ultrasound beam) using a preview image and calculate the true blood velocities. The calculation of a volumetric flow rate requires a manual measurement of the vessel cross-sectional area and assumes a certain velocity profile for the blood flow across the lumen. This technique requires several manual steps by a sonographer and is thus, impractical for continuous vascular monitoring. Thus, cross-sectional area measurements are currently performed by manually measuring the diameter in a long-axis view of the artery with a sonographer using visual feedback to maintain precise alignment of the probe with the center of the vessel. This approach requires a sonographer and is prone to alignment errors thereby, making the process impractical for continuous vascular monitoring applications.

Other methods to correct for the Doppler angle include cross-beam Doppler where multiple firing at the center of the vessel to triangulate the axial velocities into a two-dimensional (2-D) velocity vector. Again this method assumes a radial symmetric velocity profile with a specific shape, such as a parabolic profile.

Furthermore, other volumetric techniques include using blood velocity estimates in an entire volume to provide data for estimating the volumetric flow rate. One method includes integrating the velocity over a curved surface to remove the dependency of the volumetric flow rate measurement on Doppler angle. Another method includes using the 3-D blood velocity estimates to define the centerline in a volume. Neither of these methods that utilize volumetric acquisition are suitable for producing continuous waveforms over the cardiac period because of the long acquisition time for the volumetric color flow frames and the potential for significant motion over the frame time.

Accordingly, there exists a need for efficient non-invasive continuous monitoring of patient parameters in real-time.

BRIEF DESCRIPTION

In accordance with an embodiment of the invention, a method for continuous non-invasive monitoring of multiple arterial parameters of a patient is provided. The method includes acquiring continuously measured ultrasound data via an ultrasound transducer attached to the patient for detecting a blood vessel using color flow processing within a monitoring scan plane. Further, the method includes processing the continuously measured ultrasound data to generate continuous quantitative waveforms based on an estimated cross-sectional area of the blood vessel and an estimated volumetric flow rate of blood through the vessel and displaying the generated continuous quantitative waveforms for monitoring the arterial parameters of the patient in real-time.

In accordance with an embodiment of the invention, a method for continuous non-invasive monitoring of multiple arterial parameters of a patient is provided. The method includes acquiring continuously measured ultrasound data via an ultrasound transducer attached to the patient for detecting a blood vessel through a short-axis view and using color flow processing within a monitoring scan plane. The method also includes determining a centerline of the blood vessel through a volume using data from multiple tracking scan planes. Further, the method includes determining a blood flow direction along the centerline, estimating a Doppler angle and a flow angle for the monitoring scan plane, checking if the Doppler angle is above or below a threshold value and adjusting the tilt of the monitoring scan plane, estimating a contour of the blood vessel within the monitoring scan plane using a B-mode image, estimating a cross-sectional area of the blood vessel based on the estimated contour and the centerline of the blood vessel and reducing noise in two-dimensional blood velocity estimates obtained from the color flow processing. The method includes estimating a volumetric flow rate of blood from the two-dimensional blood velocity estimates within the monitoring scan plane, the centerline and the contour of the blood vessel. Further, the method includes updating the centerline within a volume of the blood vessel using data from the plurality of tracking scan planes and generating continuous quantitative waveforms based on the cross-sectional area of the blood vessel and the volumetric flow rate of blood through the vessel. Finally, the method includes displaying the generated continuous quantitative waveforms for monitoring the arterial parameters of the patient in real-time.

In accordance with an embodiment of the invention, a system for continuous non-invasive monitoring of multiple arterial parameters of a patient is provided. The system includes an ultrasound imager and an ultrasound transducer acoustically coupled to the patient for acquiring a plurality of ultrasound data. The system also includes an ultrasound processor coupled to the ultrasound transducer. The ultrasound processor is configured to detect a blood vessel through a short-axis view and using a color flow processing within a monitoring scan plane, determine a centerline of the blood vessel through a volume using data from a plurality of tracking scan planes, determine a blood flow direction along the centerline, estimate a Doppler angle and a flow angle for the monitoring scan plane, check if the Doppler angle is above or below a threshold value and adjust the tilt of the monitoring scan plane, estimate a contour of the blood vessel within the monitoring scan plane using a B-mode image, estimate a cross-sectional area of the blood vessel based on the estimated contour and the centerline of the blood vessel. The ultrasound processor is also configured to reduce noise in two-dimensional blood velocity estimates obtained from the color flow processing, estimate a volumetric flow rate of blood from the two dimensional blood velocity estimates within the monitoring scan plane, the centerline and the contour of the blood vessel. The ultrasound processor is further configured to update the centerline within a volume of the blood vessel using data of the plurality of tracking scan planes. Finally the system includes a display coupled to the processor and said display is configured to output a continuous quantitative waveforms based on the cross-sectional area of the blood vessel and the volumetric flow rate of blood.

In accordance with another embodiment of the invention, a method of processing continuously measured ultrasound data of a patient is provided. The method includes receiving the continuously measured ultrasound data acquired via an ultrasound transducer attached to the patient for detecting a blood vessel through a short-axis view and using color flow processing within a monitoring scan plane. The method also includes determining a centerline of the blood vessel through a volume using data from multiple tracking scan planes. Further, the method includes determining a blood flow direction along the centerline, estimating a Doppler angle and a flow angle for the monitoring scan plane, checking if the Doppler angle is above or below a threshold value and adjusting tilt of the monitoring scan plane, estimating a contour of the blood vessel within the monitoring scan plane using a B-mode image, estimating a cross-sectional area of the blood vessel based on the estimated contour and the centerline of the blood vessel and reducing noise in the two-dimensional blood velocity estimates obtained from the color flow processing. The method includes estimating a volumetric flow rate of blood from the two dimensional blood velocity estimates within the monitoring scan plane, the centerline and the contour of the blood vessel. Further, the method includes updating the centerline within a volume of the blood vessel using data of the plurality of tracking scan planes and finally generating continuous quantitative waveforms based on the cross-sectional area of the blood vessel and the volumetric flow rate of blood through the vessel.

DRAWINGS

These and other features, aspects, and advantages of the present invention will become better understood when the following detailed description is read with reference to the accompanying drawings in which like characters represent like parts throughout the drawings, wherein.

Figure 8:
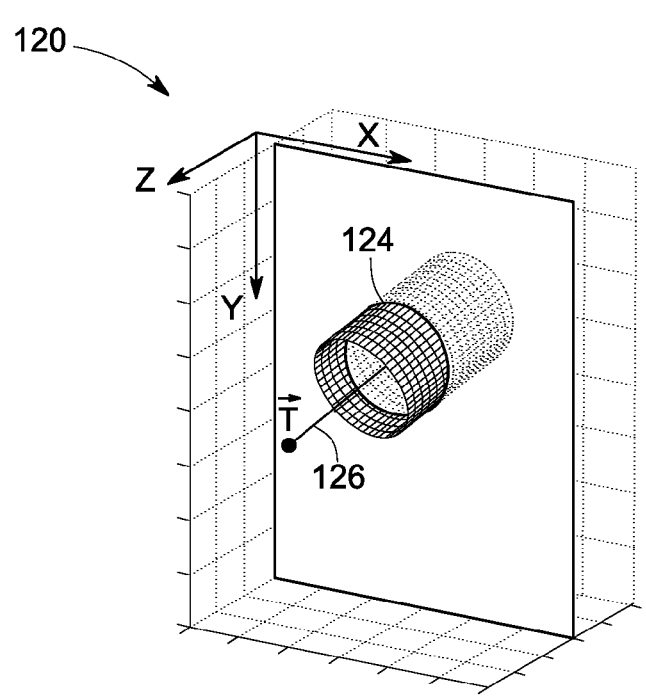
FIG. 8 shows an intersection of a vessel with the monitoring scan plane in accordance with another embodiment of the invention.
Figure 8:
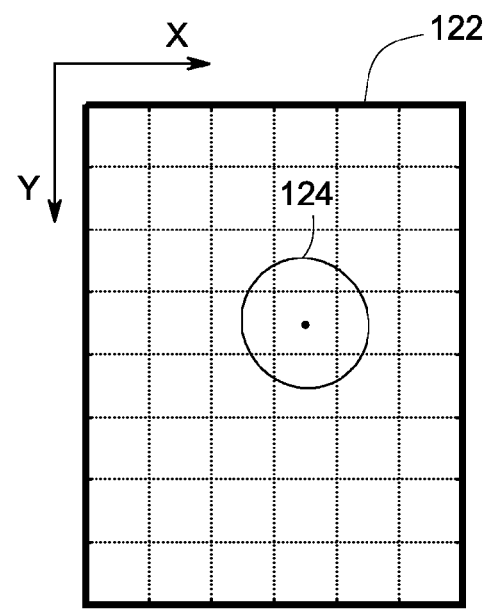
Figure 9:
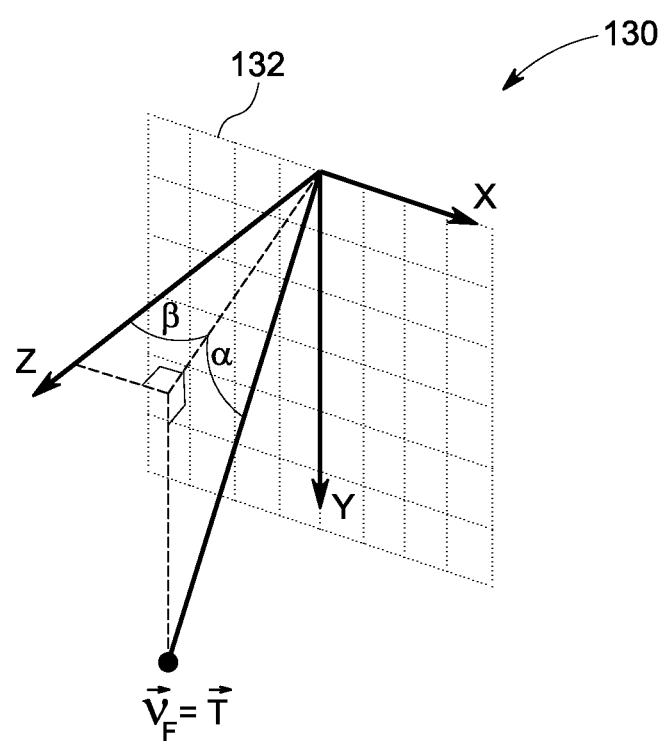

FIG. 9 defines the rotation angles that define the orientation of the vessel shown in FIG. 8 in accordance with an embodiment of the invention.

Figure 10:
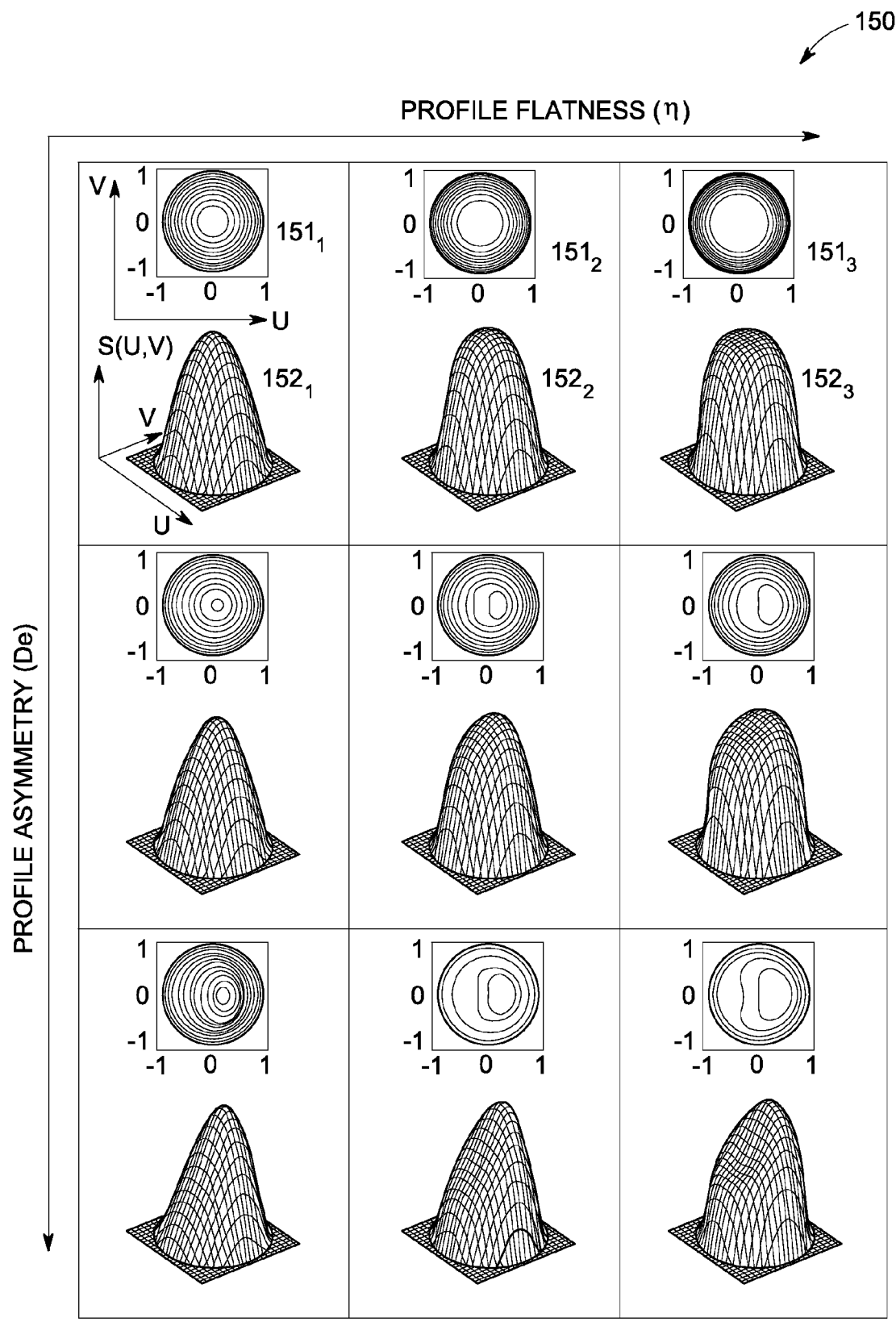

FIG. 10 shows several examples of axially symmetric and asymmetric flow profiles in accordance with an embodiment of the invention.

Figure 11:
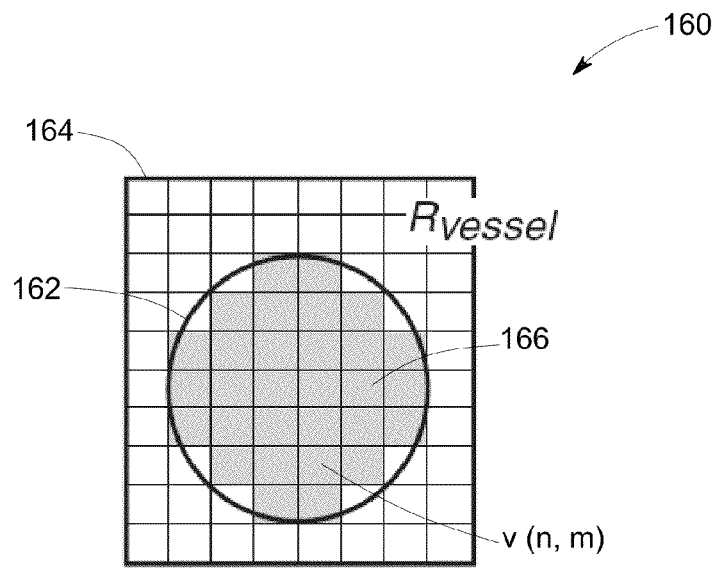

FIG. 11 illustrates a 2-D color flow pixels within the lumen of the vessel to use in the calculation of a volumetric flow rate in accordance with an embodiment of the invention.

Figure 12:
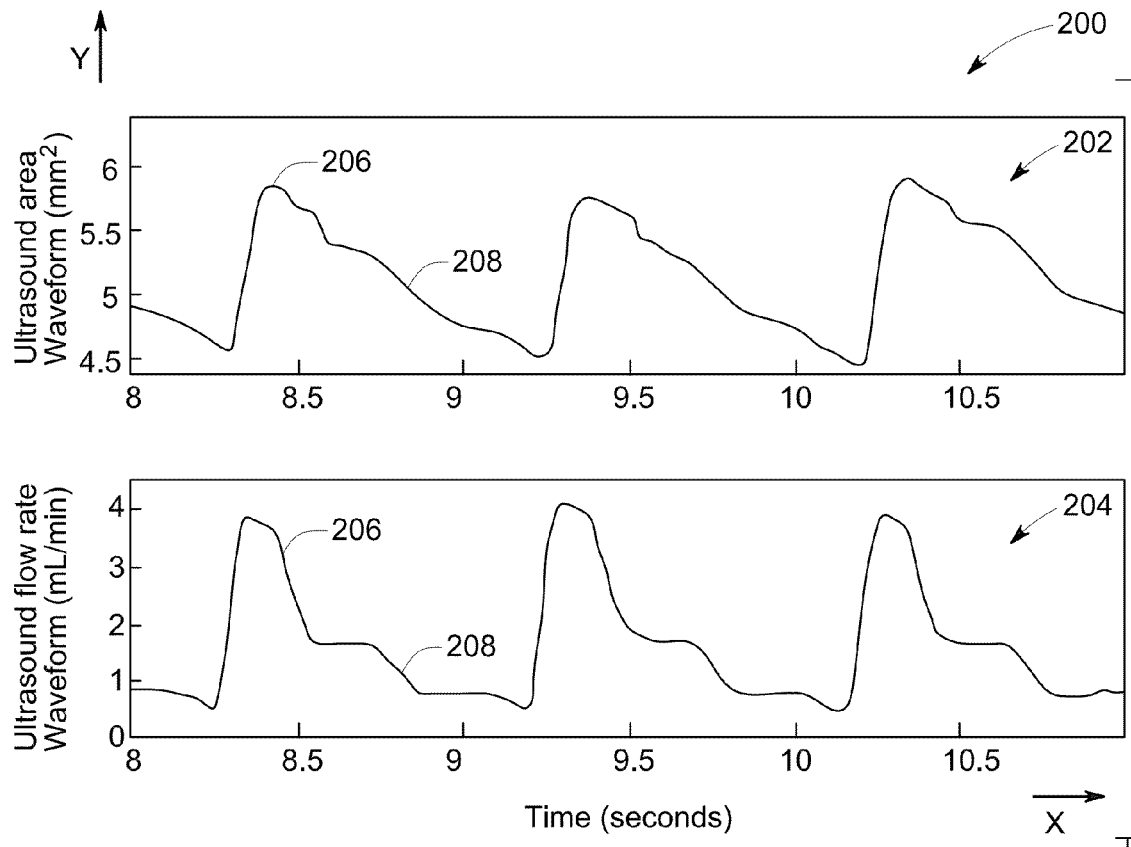

FIG. 12 is an illustration of continuous arterial waveforms of cross-sectional area and volumetric flow rate depicted on a real-time pulse display.

DETAILED DESCRIPTION

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements. Further, the term 'processing' may refer to reading or recording or rewriting or retrieving of data from a data storage system. Any examples of operating parameters are not exclusive of other parameters of the disclosed embodiments.

Figure 1:
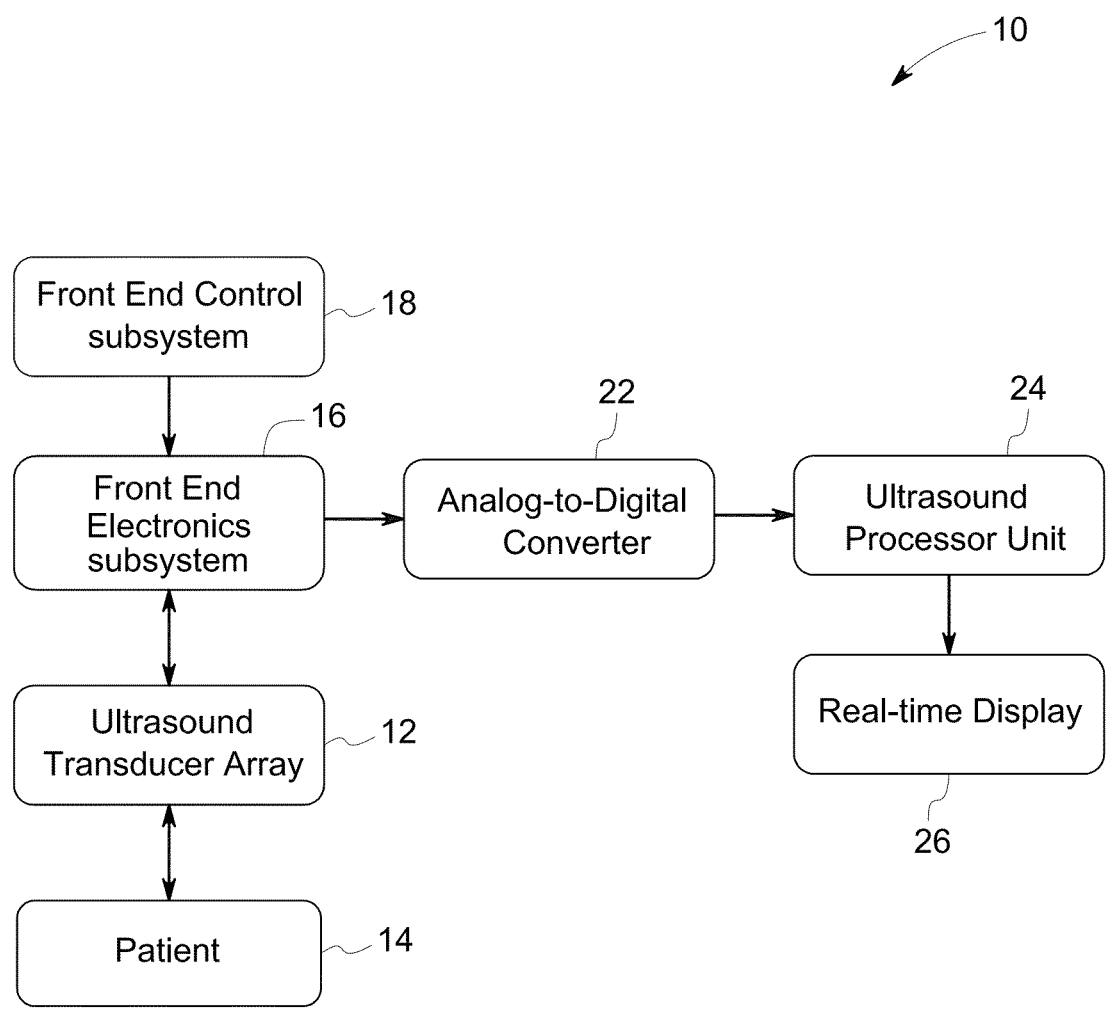
FIG. 1 is a block diagram representation of a system for continuous non-invasive monitoring of the arterial parameters of a patient in accordance with an embodiment of the invention.

FIG. 1 is a block diagram illustrating various components of an ultrasound-based patient monitoring system 10 in accordance with an embodiment of the invention. The system 10 includes an ultrasound transducer array 12 that is in contact with a patient 14 and acoustically coupled using an ultrasound gel for continuously acquiring ultrasound data. Further, the ultrasound transducer array 12 is connected to an electronic front-end subsystem 16, which electronic front-end subsystem 16 is operated by a front-end control subsystem 18 that controls the timing and scanning of transmitted and received ultrasound signal beams 20. The received ultrasound signal beam 20 contains multiple ultrasound data, which is sampled using an analog to digital converter 22. Furthermore, the ultrasound data is sent to a back-end ultrasound-processor unit 24. The ultrasound processor unit 24 performs the calculations on the ultrasound data to produce arterial waveforms that are sent to a real-time pulse display monitor 26.

In one embodiment, the ultrasound transducer array 12 continuously acquires ultrasound data for detecting a blood vessel of the patient through a short-axis view and using color flow processing within a monitoring scan plane. This includes interleaving a high frame rate two-dimensional data acquisition confined to a single monitoring scan plane with a slow frame rate two-dimensional data acquisition from one or more tracking scan planes covering a volume containing a segment of the blood vessel. Further, the high frame rate two-dimensional data acquisition within the single monitoring scan plane includes a two-dimensional color flow-imaging mode having a B-mode image sequence and a color flow image sequence. Also, the slow frame rate ultrasound data acquisition from the one or more tracking scan planes includes a B-mode imaging mode or a two-dimensional color flow imaging mode having a B-mode image sequence and a color flow image sequence. In one embodiment, the monitoring scan plane and the one or more tracking scan planes are formed by electronically steering ultrasound beams within the scan planes generated using the ultrasound transducer array 12, wherein said ultrasound transducer array 12 includes using a single two-dimensional array of ultrasound transducer elements or a plurality of linear arrays of ultrasound transducer elements spatially offset from each other to cover a volume.

Figure 2:
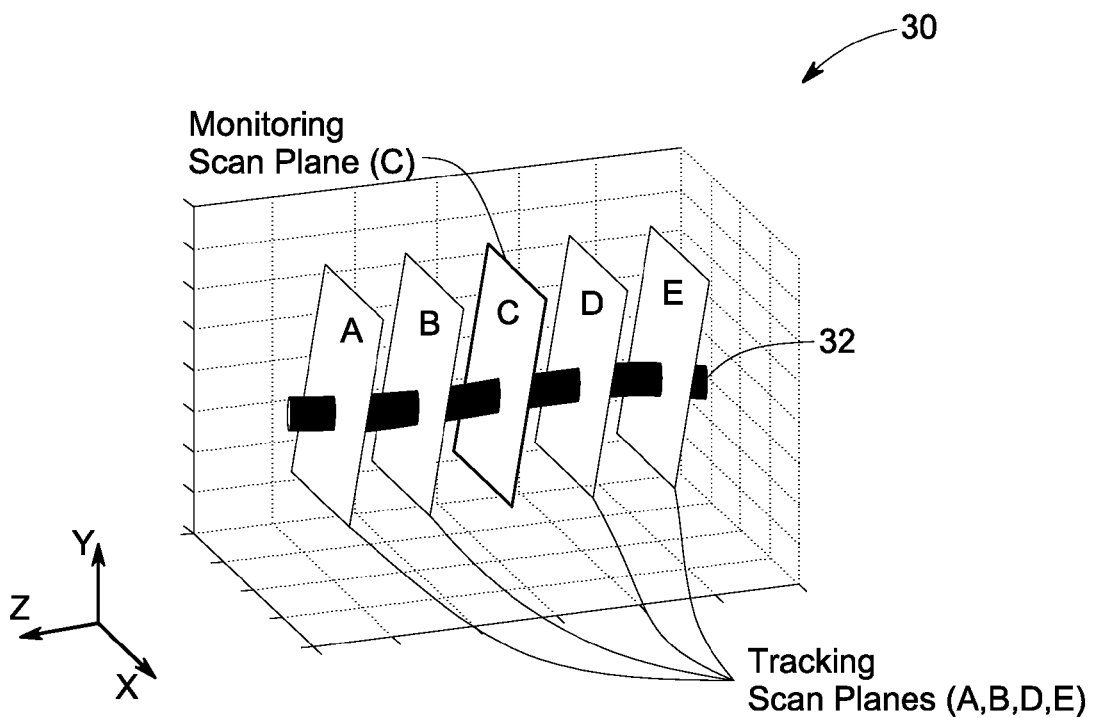
FIG. 2 shows a non-limiting example of a multi-plane acquisition method for the ultrasound-based monitoring system in accordance with an embodiment of the invention.

FIG. 2 shows a non-limiting example of a multi-plane acquisition method 30 for ultrasound-based patient monitoring system 10 (as shown in FIG. 1) in accordance with an embodiment of the invention. As shown, the multi-plane acquisition includes five parallel scan planes (A, B, C, D, E) with a constant tilt angle intersecting a blood vessel 32. This configuration is achieved with separate linear arrays offset from each other. In the present non-limiting example, the middle scan plane (C) is the high frame rate monitoring scan plane for generating the continuous waveforms, and the remaining scan planes (A, B, D, E) are tracking scan planes used for tracking the vessel location and determining the vessel orientation.

Figure 3:
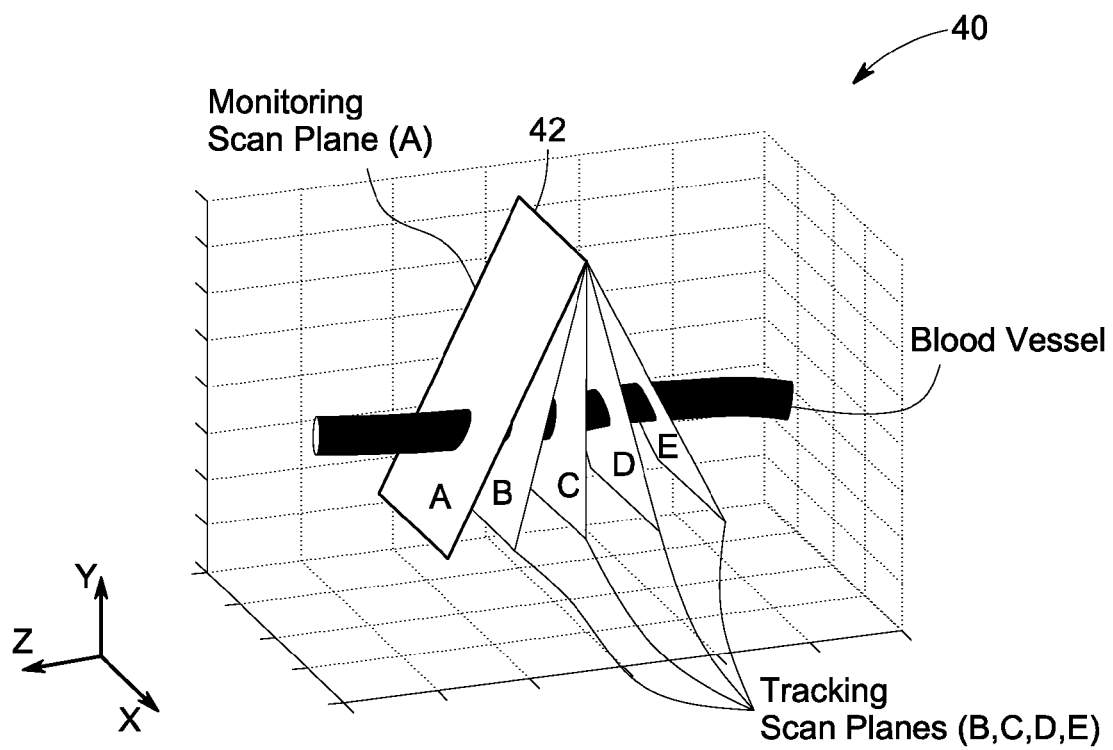
FIG. 3 shows a non-limiting example of a multi-plane acquisition method for ultrasound based monitoring system in accordance with another embodiment of the invention.

FIG. 3 shows another non-limiting example of a multi-plane acquisition method 40 for ultrasound based patient monitoring system 10 (as shown in FIG. 1) in accordance with another embodiment of the invention. As shown, the multi-plane acquisition includes five scan planes (A, B, C, D, E) rotated around a fixed axis 42 and intersecting the blood vessel. This configuration is achieved with multiple elevation slices from a single two-dimensional phased array. It is to be noted that the monitoring scan plane in this example is scan plane A.

Figure 4:
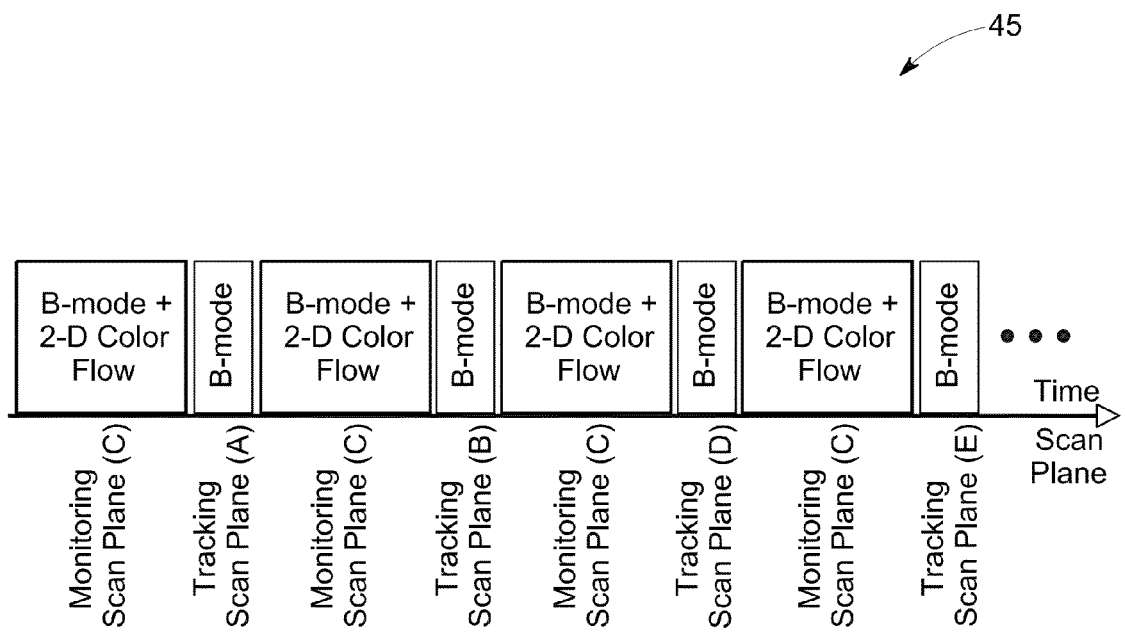
FIG. 4 is a non-limiting example of a scan sequence method for the multi-plane acquisition shown in FIG. 2 and FIG. 3 in accordance with an embodiment of the invention.

FIG. 4 is a non-limiting example of a scan sequence 45 for multi-plane acquisition method as shown in FIG. 2 in accordance with an embodiment of the invention. B-mode plus two-dimensional color flow frames are acquired in the monitoring scan plane (C) (shown in FIG. 2) at a fixed rate. A B-mode frame or B-mode plus 2-D color flow frame from one of the tracking scan planes (A, B, D, E as shown in FIG. 2), is interleaved between the monitoring frames. The scan sequence is repeated after a frame from each of the tracking scan planes has been acquired. In this non-limiting example, the frame rate for the individual tracking scan planes is one-fourth the frame rate of the monitoring scan plane.

As discussed, the ultrasound processor 24 (shown in FIG. 1) is thus, configured to process the received ultrasound data to detect the blood vessel through the short-axis view and using color flow processing within the monitoring scan plane. Moreover, in accordance with an embodiment of the present invention, the ultrasound processor 24 (shown in FIG. 1) processes the ultrasound data with respect to an algorithm as shown in FIG. 5.

Figure 5:
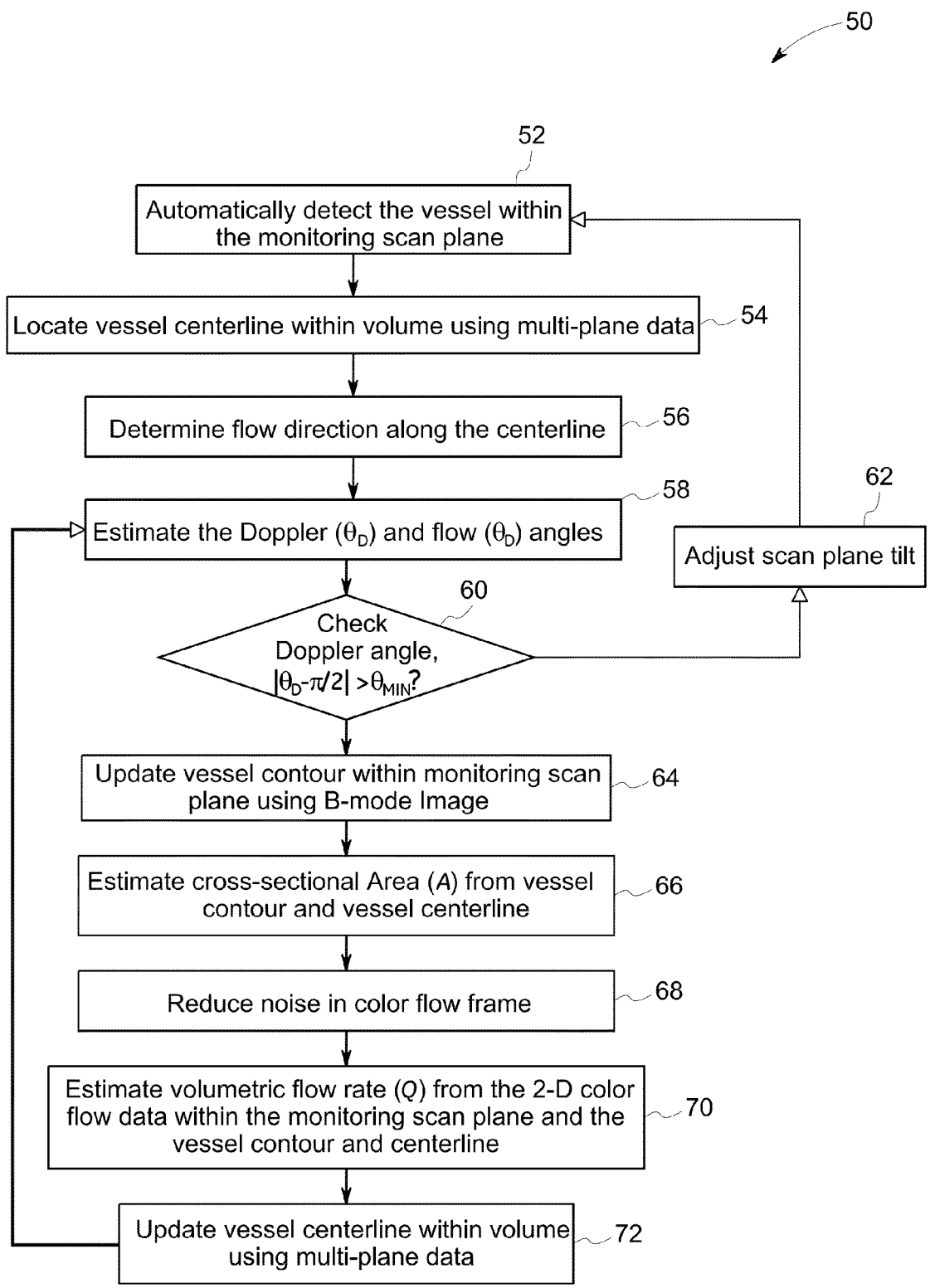
FIG. 5 is a block diagram of the processing blocks for generating the quantitative arterial measurements from the multi-plane ultrasound data in accordance with an embodiment of the invention.

FIG. 5 is a block diagram 50 of the processing steps carried out by the ultrasound processor 24 (as shown FIG. 1) for generating the quantitative arterial measurements from multi-plane ultrasound data in accordance with an embodiment of the invention. At step 52, the processing starts with automated detection of the blood vessel within the monitoring scan plane and the tracking scan planes (as shown in FIG. 2 and FIG. 3). The processing step 54 also includes determining a centerline of the blood vessel through a volume using data from the plurality of tracking scan planes. Further at step 56, a blood flow direction along the vessel centerline is determined from the vessel locations in the multiple planes and the orientation of the blood vessel relative to the monitoring scan plane is estimated from the centerline. At step 58, a Doppler angle and a flow angle for the monitoring scan plane is estimated and a check of the magnitude of the Doppler angle is performed at step 60. Based on the checked value of the Doppler angle above or below a threshold value, the monitoring scan plane is adjusted by tilting at step 62. Further, a contour of the blood vessel within the monitoring scan plane using a B-mode image is estimated. For each new frame, the location of the blood vessel in the monitoring and tracking planes (as shown in FIG. 2 and FIG. 3) is updated at step 64. Further at step 66, the cross-sectional arterial area is estimated from the contour of the vessel in the monitoring scan plane and the vessel orientation (the centerline of the blood vessel). Furthermore, a two-dimensional blood velocity estimates is smoothed to reduce noise at step 68. At step 70, a volumetric flow rate of blood is estimated from the data, the noise effects in which have already been reduced by the smoothening of the two-dimensional blood velocity estimates within the monitoring scan plane, the vessel contour and the vessel centerline. At step 72, the vessel centerline is updated using the current vessel locations within the multiple tracking scan planes. The process is repeated for each new frame of data that is acquired. Finally, the continuous quantitative waveforms are generated based on the estimated cross-sectional area of the blood vessel and the estimated volumetric flow rate of blood. Each of the above processing steps is further discussed is details below.

The processing of the ultrasound data begins with the automated detection (step 52 of FIG. 5) of the blood vessel or artery within the monitoring scan plane and the tracking scan planes (as shown in FIG. 2 and FIG. 3). When the ultrasound transducer array 12 (as shown in FIG. 1) is placed over a blood vessel, the blood vessel is automatically found using the two-dimensional color flow image sequence taken in the monitoring scan plane as discussed in FIG. 2, FIG. 3 and FIG. 4. From the location of the blood vessel, the edge of the blood vessel is detected using a matched filter approach that defines the contour of the blood vessel in the monitoring scan plane and each of the plurality of tracking scan planes. In one embodiment, the contour is specified as an arbitrary shape using a series of points within the monitoring or tracking scan plane, $$\{(x_1^{(M)}, y_1^{(M)}), (x_2^{(M)}, y_2^{(M)}), K, (x_{N_M}^{(M)}, y_{N_M}^{(M)})\}$$

where $x_i^{(M)}$ is the horizontal position, $y_i^{(M)}$ is the vertical position for the $i^{th}$ point on contour, $N_M$ is the number of contour points, and M indicates these points are for the monitoring scan plane.

In another embodiment, the contour is specified as a shape and the contour defined by a set of shape parameters. For example, if the contour shape is an ellipse, the contour is specified by a set of five parameters defining the location, size, and orientation of the ellipse within the scan plane according to one embodiment.

Figure 6:
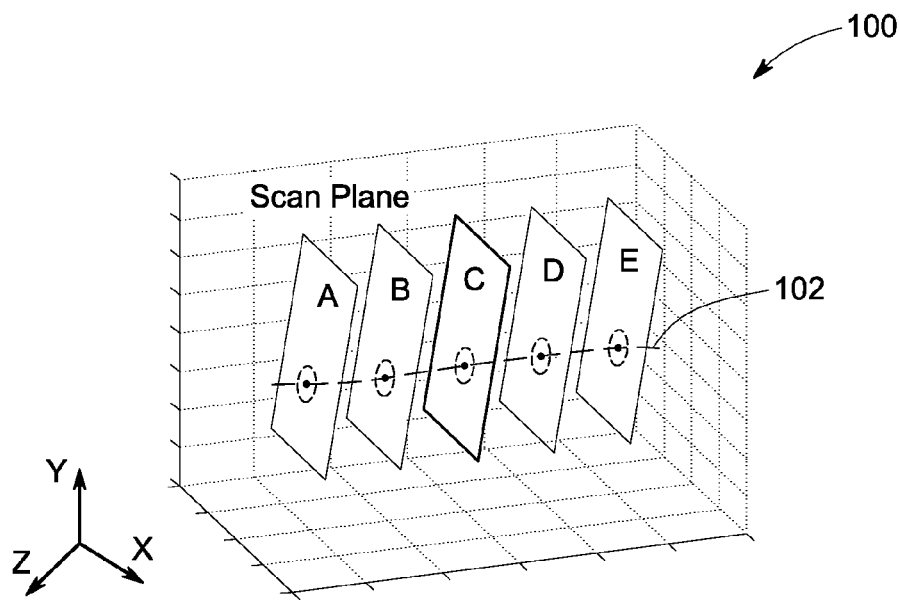
FIG. 6 illustrates the 3-D model of the vessel centerline determined from the locations of the vessel within the ultrasound scan planes for the multi-plane example in FIG. 3 and FIG. 4.

FIG. 6 illustrates a three-dimensional (3-D) model 100 of a blood vessel centerline 102 determined from the locations of the vessel within the scan planes for the multi-plane acquisition methods in FIG. 3 and FIG. 4. As shown, the 3-D model 100 includes five parallel scan planes (A, B, C, D, E) with a constant tilt angle intersecting a blood vessel. It is to be noted that the middle scan plane (C) is the high-frame-rate monitoring scan plane for generating the continuous waveforms, and the remaining scan planes (A, B, D, E) are tracking scan planes used for tracking the vessel location and determining the vessel orientation. The centers of the blood vessel in the scan planes and the position of the scan planes in 3-D are used to estimate the parameters of a centerline curve 102. This processing step of determining the vessel centerline 102 (step 54 of FIG. 5) includes estimating the contour of the vessel in each scan plane, determining the blood vessel center coordinate in each scan plane (A, B, C, D, E) from the contour, converting the center locations into a common coordinate system, and fitting a curve to the centerline points in 3-D space. Further, an area of the contour of the blood vessel within the monitoring scan plane is converted to a cross-sectional area using the direction of the vessel centerline at the point where the centerline intersects the monitoring scan plane.

The same procedure used to find the vessel location in the monitoring scan plane (C) is used to find the vessel contours in the other scan planes from the B-mode and 2-D color flow image sequences for the scan planes. The center of the vessel is calculated from the contour. For an arbitrary shape with points equally spaced around the contour, the vessel center is calculated as an average of the contour points:

$$xc_A^{(A)} = \frac{1}{N_A} \sum_{i=1}^{N_A} x_i^{(A)} \text{ and } yc_A^{(A)} = \frac{1}{N_A} \sum_{i=1}^{N_A} y_i^{(A)},$$

while for a specified shape, such as an ellipse, the center is determined directly from the contour parameters.

The location of center points in each of the scan planes (A, B, C, D, E) are converted to single common coordinate frame using knowledge of the orientation of the scan planes relative to the coordinate system. The coordinate transform can be implemented using a transformation matrix. For example, the transformation of the center point from the scan plane A to the monitoring scan plane C can be written by:

$$\begin{bmatrix} xc_A^{(M)} \\ yc_A^{(M)} \\ zc_A^{(M)} \\ 1 \end{bmatrix} = R_{A2M} \begin{bmatrix} xc_A^{(A)} \\ yc_A^{(A)} \\ 0 \\ 1 \end{bmatrix}$$

where $R_{A2M}$ is a [4×4] homogeneous transformation matrix that combines translation and rotation when applied to the homogeneous coordinate with one on the last element. The z component of the vessel center was zero in the original scan plane, but the z component will not be zero in the transformed coordinate system.

The curve representing the vessel centerline 102 is determined from the vessel center points. The curve can be parameterized a polynomial to each of the three spatial components using regression techniques. The components of the centerline curve are parameterized as $$x_{CL}^{(M)}(s) = p_{x0} + p_{x1}s + \Lambda + p_{xr}s^r;$$

$$y_{CL}^{(M)}(s) = p_{y0} + p_{y1}s + \Lambda + p_{yr}s^r; \text{ and}$$

$$z_{CL}^{(M)}(s) = p_{z0} + p_{z1}s + \Lambda + p_{zr}s^r$$

where, the p's are the coefficients of the polynomials, r is the order of the polynomial, and $0 \le s \le 1$.

Furthermore, the processing step of 56 (as shown in FIG. 5) includes determining the direction of flow along the vessel centerline determined from the vessel locations in the multiple scan planes, and estimating the orientation of the vessel relative to the monitoring scan plane C from the vessel centerline 102 (as shown in FIG. 6). The 3-D direction of the blood flow is determined by the direction that the blood vessel crosses the monitoring scan plane C. The tangent to the centerline at the monitoring scan plane C provides a good estimate of the average flow direction for relatively straight vessels. The tangent vector to the centerline 102 is given by $$\vec{t}(s) = \begin{bmatrix} dx_{CL}^{(M)}/ds \\ dy_{CL}^{(M)}/ds \\ dz_{CL}^{(M)}/ds \end{bmatrix}$$

At the point where the centerline 102 crosses the monitoring scan plane ($s=s_M$), the flow is along either the positive or negative tangent vector, $\pm \vec{t}(s_M)$.

The direction of the average axial flow at the center of the vessel is used to determine the direction of the flow along the vessel centerline 102. A vector representing the average blood velocity along the ultrasound beam is $$\vec{v}_b = \left( \frac{1}{N_{frames}} \sum_{p=1}^{N_{frames}} V_{CF}(n_c, m_c, p) \right) \vec{b}$$

where $\vec{b}$ is the direction of the ultrasound beam and $V_{CF}$ (n, m, p) is the axial projection of the blood velocity from the color flow image for the $n^{th}$ row, $m^{th}$ column, and $p^{th}$ frame with positive axial flow defined toward the ultrasound transducer. The average axial velocity vector is then projected onto the tangent vector and the sign of the projection is used to determine the flow direction. The unit vector in the direction of the flow is $$\vec{v}_F = \text{sgn}(\vec{v}_{axial} \cdot \vec{t}(s_M)) \frac{\vec{t}(s_M)}{|\vec{t}(s_M)|}$$

where sgn( ) is the sign operator.

Figure 7:
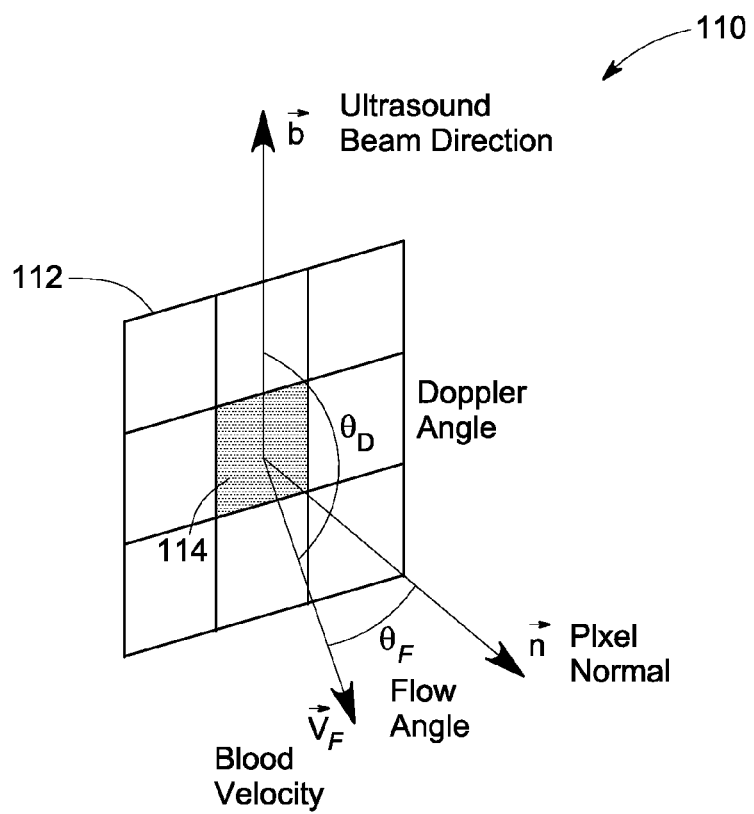
FIG. 7 is an illustration defining the Doppler and flow angles relative to a pixel in the monitoring scan plane in accordance with another embodiment of the invention.

FIG. 7 is an illustration 110 defining a Doppler angle and flow angle relative to a pixel 114 in the monitoring scan plane 112 in accordance with another embodiment of the invention. As discussed, the processing step 58 (as shown in FIG. 5) includes estimating the Doppler angle, $\theta_D$ and the flow angle, $\theta_F$ for the monitoring scan plane 112. FIG. 7 shows the Doppler angle, $\theta_D$ as the angle between the ultrasound beam direction, $\vec{b}$, and the blood velocity direction, $\vec{v}_F$, which is taken as the axial flow direction. The flow angle $\theta_F$ is the angle between the pixel normal, $\vec{h}$, and the blood velocity direction $\vec{v}_F$. Thus, the Doppler and flow angles are calculated from the vectors for the ultrasound beam direction, the pixel normal, and the flow direction. These angles are estimated by $$\theta_D = \cos^{-1}(\vec{b} \cdot \vec{v}_F) \text{ and } \theta_F = \cos^{-1}(\vec{h} \cdot \vec{v}_F)$$

where $\vec{b}$ is a unit vector in the beam direction of the ultrasound beam pointing toward the transducer, $\vec{h}$ is the unit normal vector for the pixel, and $\vec{v}_F$ is the unit vector along the flow direction.

Further, the processing step of 60 (as shown in FIG. 5) includes checking of the magnitude of the Doppler angle, $\theta_D$. A minimum Doppler angle is required for a sufficient percentage of the blood velocities above the cutoff velocity of the wall filter to provide an accurate volumetric flow rate estimation. If the Doppler angle is below a threshold for the minimum Doppler angle, the monitoring scan plane 112 is adjusted or tilted as shown in step 62 (as shown in FIG. 5). It is to be noted that for a multi-array design, the monitoring scan plane is selected from any of the individual arrays while for an electronically steered 2-D array the monitoring scan plane is positioned to a desired location and orientation in accordance with an embodiment of the invention.

FIG. 8 shows an intersection 120 of a vessel with the monitoring scan plane 122 in accordance with an embodiment of the invention. As shown, the vessel contour 124 is within the monitoring scan plane 122 for a short straight segment of the circular vessel. The vessel contour 124 intersects the monitoring scan plane 122 at an oblique angle. The vessel contour 124 within the scan plane may have an elliptical shape and hence the orientation of the vessel is defined by a centerline tangent 126 to the vessel centerline, T. This provides input into the processing of the step 66 (as shown in FIG. 5) whereby, the cross-sectional area is estimated from the contour 124 of the vessel in the monitoring scan plane 122 and the vessel orientation. In one embodiment, the vessel area within the monitoring scan plane 122 is converted to an estimate of the cross-sectional area assuming a right circular cylinder model of the vessel and the orientation of the vessel relative to the scan plane.

FIG. 9 illustrates the orientation 130 of the blood vessel relative to the monitoring scan plane 132 in the x-y plane in accordance with an embodiment of the invention. As shown, the vessel centerline $\vec{T}$ coincides with the blood velocity unit vector $\vec{v}_F$. The rotation angles $\alpha$ and $\beta$, define the orientation of the blood vessel (shown in FIG. 8) relative to the monitoring scan plane 132 (shown as 122 in FIG. 8) and are given by $$\alpha = \cos^{-1}\left(\sqrt{1-v_y^2}\right) \text{ and}$$

$$\beta = \cos^{-1}\left(\frac{v_z}{\sqrt{1-v_y^2}}\right)$$

where $v_y$ and $v_z$ are the y and z components of the unit flow vector, $\vec{v}_F = [v_x\ v_y\ v_z]^T$. The area within the monitoring scan plane 122 is converted into an estimate of the cross-sectional area by $$\hat{A} = (\Delta_x \Delta_y \cos \alpha_v \cos \beta_v) A_{MSP}$$

where $\Delta_x$ and $\Delta_y$ are the pixel dimension in the x and y axes respectively, $\alpha$ and $\beta$ are the rotation angles, and $A_{MSP}$ is the area of vessel contour within the monitoring scan plane in accordance with an embodiment of the invention.

Further, in the processing step 68 (as shown in FIG. 5) the blood velocity estimates are smoothed to reduce noise. The mean velocity estimates from the color flow processing contain noise and the property of the noise will depend on the mean velocity with the highest noise levels for low velocities that fall below the cutoff for the wall filter. To reduce the impact of color flow noise on the volumetric flow rate estimation, noise reduction is applied to the mean velocities estimate. Additional parameters from the color flow processing, such as color power and variance of the velocity estimate, and the B-mode brightness level provide information for estimating the noise level for individual pixels.

The spatial correlation of the velocities and the location of the vessel wall also provide information for reducing noise in the mean velocity estimates. A method for reducing the noise using the spatial correlation that is based on a model of the two-dimensional velocity profile across the lumen is described. The model utilizes a family of profiles for the axial velocity along the vessel's centerline and a contour of the vessel wall at which the velocity is zero The shape model is defined by a set of shape parameters, $\Psi$, and a mapping function, $S(u,v): \Psi \rightarrow \mathfrak{R}^3$, that defines a surface corresponding to blood velocities along the vessel axis for a set of normalized spatial coordinates, (u, v), within the cross-sectional plane.

The flow profile observed in a straight vessel is axially symmetric and for typical blood flow conditions in healthy large vessels, the Reynolds number will be low and the flow can be assumed to be laminar. A model of axially symmetric velocity profiles for laminar flow in a rigid circular tube is $$S_{symmetric}(u,v\,|\,V_{avg},\eta) = V_{peak}(1-(\sqrt{u^2+v^2}\,)^\eta)$$
$$= \frac{V_{avg}(\eta+2)}{\eta}(1-(\sqrt{u^2+v^2}\,)^\eta)$$

where u and v are the spatial components in the cross-sectional plane normalized by the vessel radius for a vessel centered at u=0 and v=0, $V_{avg}$ is the average velocity across the lumen, and the exponent, $\eta$, controls the flatness of the peak of the velocity profile. A value of $\eta=2$ corresponds to fully developed laminar flow with a parabolic flow profile, while higher values of $\eta$ approach a nearly constant velocity profile resembling plug flow.

Asymmetry in the velocity profile will be observed for curved vessels. An approximation of the velocity profile for steady flow in a rigid curved tube with small curvatures is known. Such approximation equations are parameterized by dimensionless quantity called the Dean number, De, that is equivalent to the Reynolds number for a straight tube modified by the relative radius of curvature. The Dean number is given by:

$$De = \sqrt{\frac{R_v}{R_C}}\,Re$$

where $R_v$ is the vessel radius, $R_C$ is the radius of curvature, and Re is the Reynolds number. The Dean equation for the axial flow model in polar coordinates is $$S_{Dean}(r,\phi\,|\,V_{avg},De) = V_{avg}(2(1-r^2)+De^2 g(r)\cos(\phi))$$

where r is the fractional radius, $\phi$ is the polar angle, De is the Dean number, and g(r) is a polynomial in r and is given by $$g(r) = \frac{19r - 40r^3 + 30r^5 - 10r^7 + r^9}{1440}$$

The approximation is valid for small Dean numbers that correspond to small curvatures or large radius of curvatures. Although physiological flow is not steady and is the vessel wall is elastic, these above two models can be combined into a single model for the velocity profile to approximate the shape for a wide range of physiological profiles in large arteries. The combined model produces a family of shapes that include both the axially symmetric and asymmetric profiles. The first term in the Dean equation is an axially symmetric parabolic flow profile that is then modified by the second asymmetric term. The single model is formed by replacing the parabolic term in the Dean equation for axial flow with the exponent model for symmetric flow and adding a variable to rotate the peak of the asymmetrical flow since the direction of curvature is not known. The flow profile model for the axial velocity is given by $$S(r, \varphi \mid V_{avg}, \eta, De, \varphi_0) = V_{avg}\left(\frac{\eta+2}{\eta}(1-r^\eta) + De^2 g(r)\cos(\varphi - \varphi_0)\right)$$

in polar coordinates where $\phi_0$ is the rotation angle of the peak and $$S(u, v \mid V_{avg}, \eta, De, \varphi_0) = $$
$$V_{avg}\left(\frac{\eta+2}{\eta}\left(1-(u^2+v^2)^{\eta/2}\right) + De^2 g(r)\frac{u\cos(\varphi_0) + v\sin(\varphi_0)}{\sqrt{u^2+v^2}}\right)$$

in the normalized cross-sectional coordinates. FIG. 10 shows several examples of axially symmetric and asymmetric flow profiles using this model. A family 150 of 2-D velocity profiles for the axial flow in a circular vessel is shown. The top graph ($151_1$, $151_2$, $151_3$ as shown for a top panel) is a contour plot of the axial velocity and the bottom graph ($152_1$, $152_2$, $152_3$ as shown for a top panel) is a mesh plot of the same data. The 2-D profiles in FIG. 10 are parameterized by two variables, one corresponding to the flatness of the flow peak and the other corresponding to the asymmetry of the flow profile. The flatness of the peak varies from a parabolic flow profile on the left to a flat or plug profile on the right. The second variable models curvature of the vessel by introducing asymmetry of the flow profile with the velocity profile varying from radially symmetric at the top of the figure (no curvature) to increasing asymmetry toward the bottom (higher radius of curvature).

Since the blood velocity at the vessel wall will be zero, the velocity profile is constrained to be zero along the contour of vessel wall. The vessel contour in the normalized spatial coordinate system is defined to be the unit circle, $C(u,v)=\sqrt{u^2+v^2}-1=0$. The ultrasound measurements are made in the monitoring scan plane that is rotated away from this cross-sectional plane, therefore the vessel contour in the scan plane will have an elliptical shape. The ellipse parameters for the vessel contour are determined using the B-mode images. A mapping from the monitoring scan plane to the normal cross-sectional plane is defined to impose the zero velocity constraint at the vessel wall. The projection of points in the monitoring scan plane onto the normalized cross-sectional plane assuming an elliptical contour in the scan plane is given by $$u(x, y \mid a, b, x_e, y_e, \theta_e) = $$
$$\frac{(x-x_e)}{a} + \frac{a-b}{ab}\sin(\theta_e)((x-x_e)\sin(\theta_e) + (y-y_e)\cos(\theta_e))$$

and $$v(x, y \mid a, b, x_e, y_e, \theta_e) = $$
$$\frac{(y-y_e)}{a} + \frac{a-b}{ab}\cos(\theta_e)((x-x_e)\sin(\theta_e) + (y-y_e)\cos(\theta_e))$$

where x and y are the location of the point within the scan plane, a and b are the major and minor axes of the ellipse, ($x_e$, $y_e$) is the center of the ellipse, and $\theta_e$ is the tilt angle of the ellipse.

The predicted value of the ultrasound measurements for the velocity component along the ultrasound beam can now be found using the model of the velocity profile and the vessel contour. For a given set of shape parameters, $\Psi=[V_{avg},\eta,De,\phi_0]^T$, the predicted ultrasound measurements are calculated by $$\hat{D}(n,m \mid \Psi, \theta_D) = S(u(x_m, y_n), v(x_m, y_n) \mid \Psi)\cos(\theta_D)$$

where $\theta_D$ is the estimated Doppler angle given in the previous step and ($x_m$, $y_n$) is the location of the pixel within the monitoring scan plane corresponding to the $m^{th}$ row and $n^{th}$ column The next step is to find the shape parameters that best fit the velocity estimates for the current frame, $D_k$ (n, m), where k is the frame index. A method based on the maximum a posteriori estimator is described. The MAP estimator finds the values for the shape parameters that maximize the a posteriori probability $$\hat{\Psi}_k = \underset{\Psi}{\operatorname{argmax}}\left\{\frac{p(D_k \mid \Psi)p(\Psi_k)}{p(D_k)}\right\} = \underset{\Psi}{\operatorname{argmax}}\{p(D_k \mid \Psi)p(\Psi_k)\}$$

where $p(D_k|\Psi)$ is probability of the current velocity measurements given the shape parameter (also called the likelihood function), and $p(\Psi_k)$ is a prior probability of the shape parameters for the given frame.

The expected value for the shape parameters in the $k^{th}$ frame are predicted from the estimates of the shape parameters measured in the previous frames, $\{\hat{\Psi}_1, \ldots, \hat{\Psi}_{k-1}\}$ using a Kalman filter. The state variables for the Kalman filter correspond to the shape parameter along with several of their temporal derivatives. The time update step of the Kalman filter provides estimates of both the expected value of the shape parameters, $\mu_{\Psi_k}$, and the variance of the estimate, $\sigma_{\Psi_k}^2$ for the current frame based on the previous estimates. This provides the necessary information for a prior probability density function to be determined assuming the parameters are independent Gaussian random variables. The joint a prior probability density function is $$p(\Psi_k) = \frac{1}{(2\pi)^{N_s/2}|\Sigma_k|^{1/2}} e^{-\frac{1}{2}(\Psi_k - \mu_{\Psi_k})^T \Sigma_k^{-1} (\Psi_k - \mu_{\Psi_k})}$$

where $N_S$ is the number of shape parameters (in this case $N_S=4$) and $\Sigma_k$ is the covariance matrix with the standard deviations of the shape parameter along the diagonal.

The likelihood function is found by comparing the current the measured velocities $D_k$ (n, m) to the velocities from the shape model, $\hat{D}_k(n,m|\Psi)$. The variance of the ultrasound measurements will be velocity dependent and a model of the velocity variance assuming independent noise in each pixel is used to determine the likelihood function. The probability of the given measurement over a set of pixels within the lumen given the shape parameters is $$p(D_k \mid \Psi) = p(D_k \mid \hat{D}_k) = \prod_{n,m \in R_{vessel}} \frac{1}{\sqrt{2\pi}\,\sigma_v(n,m)} e^{-\frac{(D_k(n,m) - \hat{D}_k(n,m))^2}{2\sigma_v^2(n,m)}}$$

where the product is over all the pixel within the vessel and $\sigma_v^2(n,m)$ is the variance of the velocity estimate based on the predicted velocity for that pixel.

These two equations for the prior probability and the likelihood function can be substituted into the equation for the MAP estimator and the above procedure can be implemented as a sequential estimation algorithm to find the optimal shape parameters, $\hat{\Psi}_k$, using iterative numerical minimization techniques. The optimal shape parameters are then used in the measurement update step of the Kalman filter.

Smoothed versions of the axial velocities are found using the maximum likelihood estimate of the shape parameters and the mapping from the shape parameters to the velocities along the ultrasound beam $$\hat{v}_{smooth}(n,m) = \hat{D}_k(n,m|\hat{\Psi}_k).$$

Thus, reducing noise in color flow frame includes reducing noise in mean velocities from the color flow processing by estimating a noise level for individual pixels in the monitoring scan plane based on a plurality of parameters of the color flow processing comprising color power, variance of velocity estimate, B-mode brightness level, proximity to the contour of the blood vessel, and spatial correlation of the blood velocities, and reducing the impact on the volumetric flow rate estimate for pixels identified to have low velocities and high noise.

FIG. 11 illustrates a color flow image 160 in accordance with an embodiment of the invention and further highlights the use of a vessel contour 162 within a monitoring scan plane 164 to defined 2-D color flow pixels 166 within the lumen of the vessel to use in the calculation of the volumetric flow rate. As discussed in step 70 of FIG. 5, the processing includes estimating the volumetric flow rate from the noise reduced 2-D blood velocity estimates within the monitoring scan plane and the vessel contour and centerline. The volumetric flow rate through a vessel, Q, is expressed mathematically as an integral taken over a surface that intersects the blood vessel. The volumetric flow rate is defined as:

$$Q = \int\int_S \vec{v} \cdot \vec{n}_i \, dA = \int\int_S |\vec{v}| \cos(\theta_F) \, dA$$

where the vectors in the dot product are the 3-D blood velocity, $\vec{v}$, and the unit normal to the surface, $\vec{n}$, and $dA$ is an incremental area element. If the angle between these two vectors is known, then the volumetric flow rate is found from the magnitude of the blood velocity and the cosine of the flow angle, $\theta_F$.

The magnitudes of the blood velocities can be estimated from the ultrasound blood velocity estimates. The velocity measured with ultrasound is the component of the blood velocity along the direction of the ultrasound beam, either toward or away from an ultrasound probe. Therefore, knowledge of the Doppler angle, the angle between the beam direction and blood velocity vector, is needed to calculate the magnitude of the blood velocity. The magnitude of the blood velocity is found by:

$$|\vec{v}| = \frac{\vec{v}_{smooth}}{\cos(\theta_D)}$$

where $\theta_D$ is the Doppler angle and $\vec{v}_{smooth}$ is the smoothed version of the ultrasound measured velocity.

The volumetric flow rate is estimated by numerically integrating the flow in each pixel within the lumen:

$$Q = \sum_{n,m \in R_{vessel}} \frac{\cos(\theta_F[n,m]) A_{pixel}[n,m] \vec{v}_{smooth}[n,m]}{\cos(\theta_D[n,m])}$$

where $A_{pixel}$ is the area for each pixel, $\vec{v}_{smooth}$ is the measured velocity for the each pixel, and $R_{vessel}$ is the set of pixels within the lumen. The flow pixels within the lumen are identified from the results of the B-mode edge detection. For a linear scan the pixel locations are on a rectangular grid and the area for the pixel will be constant. Additionally for laminar flow, the blood velocities will be parallel and the Doppler and Flow angles for each pixel in the linear scan will be constant. For this case, the volumetric flow rate is given by $$Q = \frac{\cos(\theta_F) A_{pixel}}{\cos(\theta_D)} \sum_{n,m \in R_{vessel}} \vec{v}_{smooth}[n,m]$$

where $A_{pixel}$ is the pixel area.

As discussed, the processing step 72 of FIG. 5, includes updating the vessel centerline using the current vessel locations within the scan planes. This process step is repeated for each new frame of data that is acquired. This also includes updating the contours in the other scan planes and centerline curve to track slowly varying changes in the vessel orientation by using the techniques discussed above. Finally the real-time pulse display monitor 26 depicts the continuous quantitative waveforms based on the cross-sectional area of the blood vessel and the volumetric flow rate of blood. In one embodiment, the continuous quantitative waveforms are generated at sample rates of about 30 to about 60 frames per second over cardiac cycle.

By way of a non-limiting example, FIG. 12 illustrates continuous arterial waveforms 200 as displayed in the real-time pulse display monitor 26 shown in FIG. 1. The real-time pulse display monitor 26 (shown in FIG. 1) scrolls horizontally to maintain a user specified time window around the current measurement for monitoring short-term or long-term trends. As shown in FIG. 12, the ultrasound area waveform 202 and an ultrasound blood flow rate waveform 204 are received by the ultrasound processor 24 (shown in FIG. 1). The y-axis of the ultrasound area waveform 202 represents area in millimeter-square ($mm^2$) units and the x-axis represents time in second (s) units. Similarly, the y-axis of the ultrasound blood flow rate waveform 204 represents flowrate in milliliter per minute (ml/min) units and the x-axis represents time in second (s) units. The ultrasound area and blood flow rate waveforms 202 and 204 can be derived from Doppler images received from the ultrasound transducer array 12 (as shown in FIG. 1) and represent the variations throughout the cardiac of the blood flow through the artery and the area of the artery. However, in either case, the ultrasound waveforms 202 and 204 will include a series of waveform peaks 206 that each correspond to the systolic point in the heartbeat cycle. In addition to the waveform peaks, the ultrasound waveforms 202 and 204 also include a series of waveform valleys 208 that generally correspond to the diastolic interval within the heartbeat cycle. Additionally, beat-to-beat parameters for the mean, minimum or maximum value can be extracted for each cardiac cycle and displayed with the waveforms received from the real-time pulse-display. In this non-limiting example, the minimum, mean and maximum values for the ultrasound area waveform 202 are noted as 4.4 $mm^2$, 5.1 $mm^2$ and 5.8 $mm^2$ respectively. For the ultrasound blood flow rate waveform 204 the minimum, mean and maximum value are found to be 95 ml/min, 390 ml/min and 2.2 ml/min respectively.

Advantageously, the present method and system enables the processing of ultrasound data to generate continuous waveforms for the cross-sectional area and volumetric flow rate independent of an operator of the ultrasound system, which makes the measurements more repeatable and reproducible. Another benefit is that the approach can be applied to both a full volumetric imaging system or a simplified 3-D acquisition configuration consisting of two or more scan planes. The present invention enables processing methods for reliable area and flow measurements from a short-axis (transverse) view of the vessel; and the use of 3-D ultrasound data to provide the necessary information for correcting the single plane measurements into quantitative while not significantly impacting the sample rate for the continuous waveforms. This method and system can be effectively applied in portable ultrasound systems or a diagnostic ultrasound system or the main processing component of stand-alone ultrasound-based monitoring unit.

Furthermore, the skilled artisan will recognize the interchangeability of various features from different embodiments. Similarly, the various method steps and features described, as well as other known equivalents for each such methods and feature, can be mixed and matched by one of ordinary skill in this art to construct additional systems and techniques in accordance with principles of this disclosure. Of course, it is to be understood that not necessarily all such objects or advantages described above may be achieved in accordance with any particular embodiment. Thus, for example, those skilled in the art will recognize that the systems and techniques described herein may be embodied or carried out in a manner that achieves or optimizes one advantage or group of advantages as taught herein without necessarily achieving other objects or advantages as may be taught or suggested herein.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method of continuous non-invasive monitoring of a plurality of arterial parameters of a patient, the method comprising:
acquiring continuously measured ultrasound data via an ultrasound transducer attached to the patient for detecting a blood vessel through a short-axis view and using color flow processing within a monitoring scan plane;
determining a centerline of the blood vessel through a volume using data from a plurality of tracking scan planes;
determining a blood flow direction along the centerline;
estimating a Doppler angle and a flow angle for the monitoring scan plane;
checking if the Doppler angle is above or below a threshold value and adjusting tilt of the monitoring scan plane;
estimating a contour of the blood vessel within the monitoring scan plane using a B-mode image;
estimating a cross-sectional area of the blood vessel based on the estimated contour and the centerline of the blood vessel;
reducing noise in two-dimensional blood velocity estimates obtained from the color flow processing;
estimating a volumetric flow rate of blood from the two-dimensional blood velocity estimates within the monitoring scan plane, the centerline and the contour of the blood vessel;
updating the centerline within a volume of the blood vessel using data from the plurality of tracking scan planes;
generating continuous quantitative waveforms based on the cross-sectional area of the blood vessel and the volumetric flow rate of blood through the vessel; and
displaying the generated continuous quantitative waveforms for monitoring the arterial parameters of the patient in real-time.

2. The method of claim 1, further comprising detecting the edge of the blood vessel using a matched filter approach for determining the contour of the blood vessel wall in the monitoring scan plane and each of the plurality of tracking scan planes.

3. The method of claim 1, wherein determining the centerline comprises: estimating the contour of the blood vessel in the monitoring scan plane and each of the plurality of tracking scan planes; determining the blood vessel center coordinate in each scan plane from the contour; converting the center locations into a common coordinate system; and fitting a curve to the centerline points in three-dimensional space.

4. The method of claim 3, wherein an area of the contour of the blood vessel within the monitoring scan plane is converted to a cross-sectional area using a direction of the vessel centerline at the point where the centerline intersects the monitoring scan plane.

5. The method of claim 1, further comprising reducing noise in mean velocities from the color flow processing by estimating a noise level for individual pixels in the monitoring scan plane based on a plurality of parameters of the color flow processing comprising color power, variance of velocity estimate, B-mode brightness level and proximity to the contour of the blood vessel.

6. The method in claim 1, further comprising converting measured blood velocities along the ultrasound beam using the color flow processing to blood velocities along a center axis of the blood vessel using a direction of the vessel centerline at a point where the centerline intersects the monitoring scan plane.

7. The method of claim 5, further comprising reducing noise in the mean velocities from the color flow processing by fitting a model of a two-dimensional profile for axial blood velocities to blood velocities along the ultrasound beam estimated from the continuously measured ultrasound data using the location of the contour of the blood vessel in the monitoring scan plane and the noise level for individual pixels.

8. The method of claim 7, further comprising the use of a maximum posterior estimator to determine a plurality of optimal parameters of the two-dimensional profile that best fit the blood velocities measured with ultrasound based on recursive estimates of a probability distribution for shape parameters from a Kalman filter.

9. The method in claim 1, further comprising converting the contour of the blood vessel from the B-mode image to a contour in the color flow image within the monitoring scan plane, identifying the pixels of the color flow image within the vessel contour, calculating the component of the axial blood velocities normal to the pixels and integrating the blood velocities along the pixel normal over vessel lumen to estimate the volumetric flow rate.

10. The method of claim 1, further comprising displaying the generated continuous quantitative waveforms in real-time along with parameters extracted from the waveforms based on the cross-sectional area of the blood vessel and the volumetric flow rate of blood through the vessel.

11. The method of claim 1, wherein the continuous quantitative waveforms are generated at sample rates of about 30 to about 60 frames per second over cardiac cycle.

12. A system for continuous non-invasive monitoring of a plurality of arterial parameters of a patient comprising:
an ultrasound imager and an ultrasound transducer array adapted to acoustically couple to the patient for acquiring a plurality of ultrasound data;
an ultrasound processor coupled to the ultrasound transducer, the ultrasound processor configured to:
detect a blood vessel through a short-axis view and using a color flow processing within a monitoring scan plane;
determine a centerline of the blood vessel through a volume using data from a plurality of tracking scan planes;
determine a blood flow direction along the centerline;
estimate a Doppler angle and a flow angle for the monitoring scan plane;
check if the Doppler angle is above or below a threshold value and adjust a tilt angle of the monitoring scan plane;
estimate a contour of the blood vessel within the monitoring scan plane using a B-mode image;
estimate a cross-sectional area of the blood vessel based on the estimated contour and the centerline of the blood vessel;
reduce noise in two-dimensional blood velocity estimates obtained from the color flow processing;
estimate a volumetric flow rate of blood from the two dimensional blood velocity estimates within the monitoring scan plane, the centerline and the contour of the blood vessel; and
update the centerline within a volume of the blood vessel using data of the plurality of tracking scan planes; and
a display coupled to the ultrasound processor configured to output a continuous quantitative waveforms based on the cross-sectional area of the blood vessel and the volumetric flow rate of blood.

13. The system of claim 12, wherein the ultrasound transducer array is adapted to acoustically couple using an ultrasound gel and further said ultrasound transducer array is connected to an electronics subsystem for controlling the timing and scanning of transmit and receive ultrasound beams.

14. The system of claim 13, wherein the system comprises an analog to digital converter for sampling data received by the electronics subsystem.

15. A method of processing continuously measured ultrasound data of a patient, the method comprising:
receiving the continuously measured ultrasound data acquired via an ultrasound transducer attached to the patient for detecting a blood vessel through a short-axis view and using color flow processing within a monitoring scan plane;
determining a centerline of the blood vessel through a volume using data from a plurality of tracking scan planes;
determining a blood flow direction along the centerline;
estimating a Doppler angle and a flow angle for the monitoring scan plane;
checking if the Doppler angle is above or below a threshold value and adjusting a tilt angle of the monitoring scan plane;
estimating a contour of the blood vessel within the monitoring scan plane using a B-mode image;
estimating a cross-sectional area of the blood vessel based on the estimated contour and the centerline of the blood vessel;
reducing noise in two-dimensional blood velocity estimates obtained from the color flow processing;
estimating a volumetric flow rate of blood from the two dimensional blood velocity estimates within the monitoring scan plane, the centerline and the contour of the blood vessel;
updating the centerline within a volume of the blood vessel using data of the plurality of tracking scan planes; and
generating continuous quantitative waveforms based on the cross-sectional area of the blood vessel and the volumetric flow rate of blood through the vessel.

* * * * *

UNITED STATES PATENT AND TRADEMARK OFFICE
CERTIFICATE OF CORRECTION

PATENT NO.       : 8,622,913 B2
APPLICATION NO.  : 12/892171
DATED            : January 7, 2014
INVENTOR(S)      : Dentinger et al.

It is certified that error appears in the above-identified patent and that said Letters Patent is hereby corrected as shown below:

On the Title Page, in the Figure, for Tag "58", in Line 1, delete "flow ($\theta_D$)" and insert -- ($\theta_F$) --, therefor.

In the Drawings

In Fig. 5, Sheet 4 of 9, for Tag "58", in Line 1, delete "flow ($\theta_D$)" and insert -- ($\theta_F$) --, therefor.

In the Specification

In Column 8, Line 51, in Equation, delete "$\theta_F = \cos^{-1} \vec{h} \cdot \vec{V}_F)$," and insert -- $\theta_F = \cos^{-1}(\vec{h} \cdot \vec{V}_F)$ --, therefor.

In Column 12, Line 10, delete "column" and insert -- column. --, therefor.

In Column 13, Line 43, delete "$\vec{V}$," and insert -- $\vec{V}$, --, therefor.

In Column 14, Line 38, delete "shown in FIG. 1." and insert -- (shown in FIG. 1). --, therefor.

Signed and Sealed this
Eighth Day of July, 2014

Michelle K. Lee
*Deputy Director of the United States Patent and Trademark Office*